(12) United States Patent
Yakubovsky et al.

(10) Patent No.: US 7,939,806 B2
(45) Date of Patent: May 10, 2011

(54) NUCLEAR MEDICINE IMAGING SYSTEM HAVING ATTENUATION CORRECTION

(75) Inventors: Leonid Yakubovsky, Haifa (IL); Alexander Vaisburd, Haifa (IL)

(73) Assignee: General Electric Company, Schenectady, NY (US)

( * ) Notice: Subject to any disclaimer, the term of this patent is extended or adjusted under 35 U.S.C. 154(b) by 303 days.

(21) Appl. No.: 12/186,315

(22) Filed: Aug. 5, 2008

(65) Prior Publication Data

US 2010/0036232 A1 Feb. 11, 2010

(51) Int. Cl.
*G01N 23/08* (2006.01)
*G01T 1/166* (2006.01)
*G01T 1/167* (2006.01)

(52) U.S. Cl. .......... 250/363.04; 250/361 R; 250/363.02; 250/363.08; 378/4; 378/15

(58) Field of Classification Search .............. 250/361 R, 250/363.02–363.05, 370.09, 370.11; 378/4, 378/15, 19, 62, 193–198, 205
See application file for complete search history.

(56) References Cited

U.S. PATENT DOCUMENTS

| | | | |
|---|---|---|---|
| 5,220,588 A * | 6/1993 | Deucher et al. ................. | 378/15 |
| 7,020,233 B1 * | 3/2006 | Tybinkowski et al. ............ | 378/4 |
| 7,087,903 B2 | 8/2006 | Balan et al. | |
| 7,194,062 B2 | 3/2007 | Balan et al. | |
| 2005/0127301 A1 | 6/2005 | Balan et al. | |
| 2006/0050839 A1 | 3/2006 | Balan et al. | |
| 2006/0214108 A1 | 9/2006 | Balan et al. | |
| 2006/0285647 A1 * | 12/2006 | Yunker ......................... | 378/197 |
| 2008/0197303 A1 * | 8/2008 | Aoi et al. ................... | 250/522.1 |
| 2010/0020919 A1 * | 1/2010 | Dragan et al. .................... | 378/4 |

\* cited by examiner

*Primary Examiner* — David P Porta
*Assistant Examiner* — Casey Bryant
(74) *Attorney, Agent, or Firm* — Dean Small; The Small Patent Law Group

(57) ABSTRACT

A nuclear medicine (NM) imaging system having attenuation correction (AC) has a stationary portion having an NM rotating portion mounted thereon. At least one gamma camera head is mounted on the NM rotating portion proximate a front side of the stationary portion and is configured to be rotated about a central axis. An AC portion comprises an X-ray source mounted on an AC rotating portion. The AC rotating portion is mounted proximate a back side of the stationary portion. The X-ray source is configured to be rotated about the central axis.

21 Claims, 5 Drawing Sheets

NUCLEAR MEDICINE IMAGING SYSTEM HAVING ATTENUATION CORRECTION

BACKGROUND OF THE INVENTION

This invention relates generally to the field of nuclear medicine and more particularly to hybrid systems having gamma camera(s) and an X-ray or computed tomography (CT) system for attenuation correction of nuclear images.

Attenuation correction in nuclear medicine imaging is well known in the art. For example, X-ray or CT images may be acquired to correct the nuclear medicine images for the effect of attenuation by intervening tissue and bone of the gamma rays that are used for producing the image.

Some hybrid systems mount the gamma detectors or heads and the X-ray (or CT) portion on a single rotor. This limits the rotation speed of the CT portion, which may increase scanning time.

Also, the combination of the systems is very heavy. Some hybrid systems mount the gamma heads and the CT portion on separate gantries that are aligned with respect to each other. Having two gantries adds weight to the overall system and additional correction and/or matching may be needed between the attenuation maps and the nuclear medicine images.

BRIEF DESCRIPTION OF THE INVENTION

In one embodiment, a nuclear medicine (NM) imaging system having attenuation correction (AC) has a stationary portion having an NM rotating portion mounted thereon. At least one gamma camera head is mounted on the NM rotating portion proximate a front side of the stationary portion and is configured to be rotated about a central axis. An AC portion comprises an X-ray source mounted on an AC rotating portion. The AC rotating portion is mounted proximate a back side of the stationary portion. The X-ray source is configured to be rotated about the central axis.

In another embodiment, an NM imaging system has a stationary portion configured to have an NM rotating portion mounted thereon. The NM rotating portion is configured to extend through the stationary portion from a front side of the stationary portion to a back side. At least one of the stationary portion and the NM rotating portion is configured to support an AC rotating portion proximate a back side of the stationary portion. At least one gamma camera head is mounted on the NM rotating portion proximate a front side of the stationary portion. One of an NM retractor and an NM slip ring is mounted proximate a back side of the stationary portion.

In yet another embodiment, a method for configuring an NM imaging system having AC includes mounting an NM rotating portion on a front side of a stationary portion using an NM bearing. An AC rotating portion is mounted proximate a back side of a stationary portion using an AC bearing. The AC rotating portion is configured to be supported by one of the NM rotating portion and the stationary portion. The NM and AC rotating portions are configured to rotate independently with respect to each other.

DETAILED DESCRIPTION OF THE INVENTION

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Figure 1:
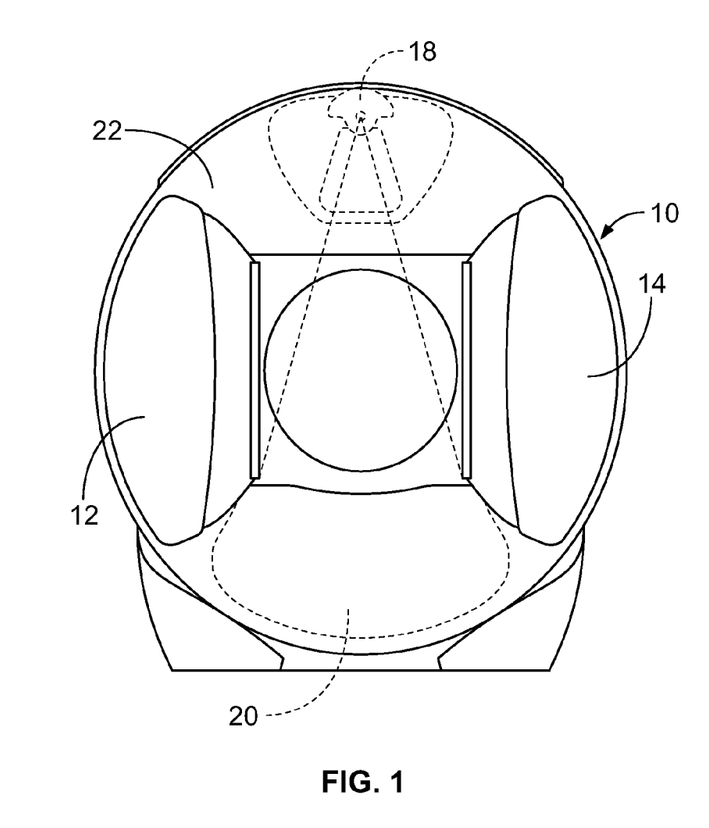
FIGS. 1 and 2 illustrate end views of a hybrid imaging system having a gamma camera or nuclear medicine system with attenuation correction (AC) formed in accordance with an embodiment of the present invention.
Figure 2:
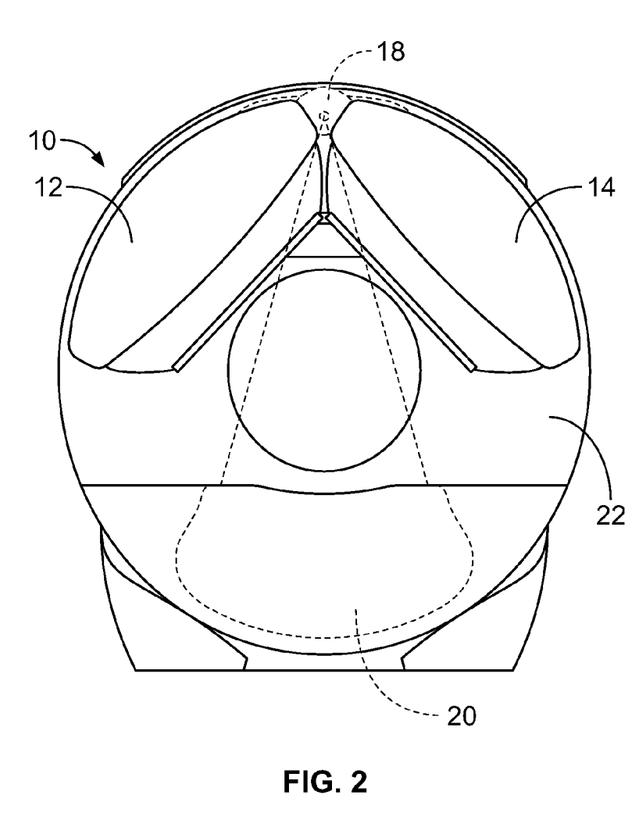
Figure 3:
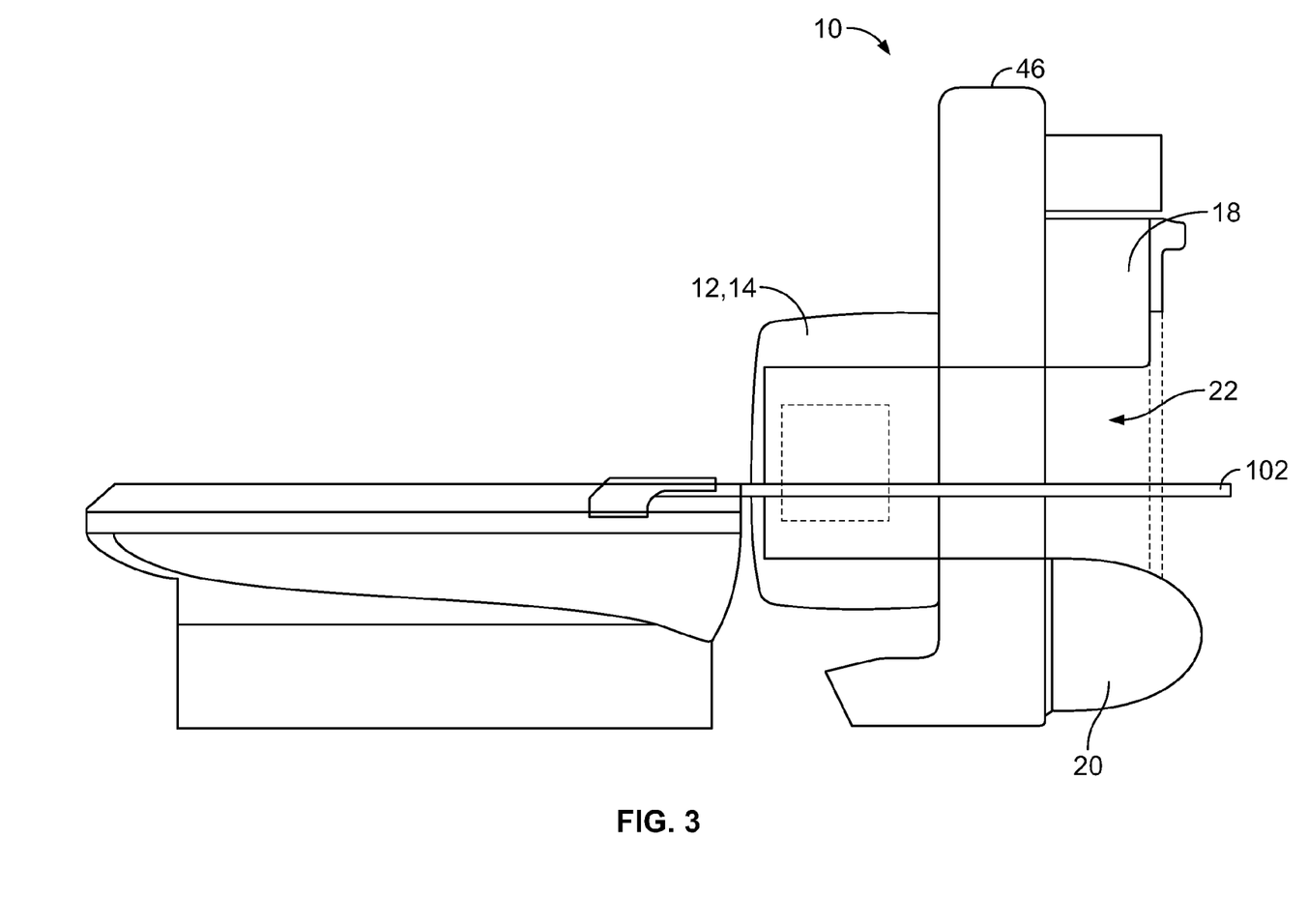
FIG. 3 illustrates a lateral view of the system of FIGS. 1 and 2 formed in accordance with an embodiment of the present invention.

FIGS. 1 and 2 illustrate end views and FIG. 3 illustrates a lateral view of a hybrid imaging system 10 having a gamma camera or nuclear medicine imaging system with attenuation correction. Imaging system 10 has a pair of gamma camera heads 12 and 14 and an X-ray imaging system that may be configured to operate as an attenuation correction (AC) imaging system. The AC imaging system may also be referred to as a CT imaging system. The AC imaging system has an X-ray source 18 and a detector 20 mounted opposite the X-ray source 18 for detecting X-rays. For example, the detector 20 may have a plurality of X-ray detectors arranged in an array. For some embodiments, only a single gamma camera head is needed. In others, three or four heads, equally spaced circumferentially about the axis of rotation, are used.

A patient (not shown) is placed on a table 102 that is advanced along a central axis that extends through an opening 22 in gantry 46. The rotation of the camera heads 12 and 14 and the X-ray source 18 and detector 20 are aligned about the central axis, which is substantially horizontal. A radio-isotope is selectively situated inside the patient, by conventional means such as via the blood stream (intravenous injection) or the lungs (inhalation) or by other means known in the art. The camera heads 12 and 14 generate nuclear imaging data signals in response to gamma rays generated by the radioisotopes. Similarly, X-ray source 18 irradiates the patient, and detector 20 generates X-ray data signals in response to the X-rays from the source 18 which impinge on the detector 20 after passing through the patient.

As shown in FIGS. 1 and 2, the angle between heads 12 and 14 is adjustable between 90 degrees and 180 degrees. Furthermore, the distance between the heads 12 and 14 may be adjusted and the transverse positions of each of the heads 12 and 14 (or of both together) may be adjusted. Alternatively, the heads 12 and 14 may be fixed at one of the positions of FIGS. 1 and 2. In yet another embodiment, three gamma camera heads may be provided, namely the two shown in FIG. 2 plus a third head, below and between the two heads shown.

Figure 4:
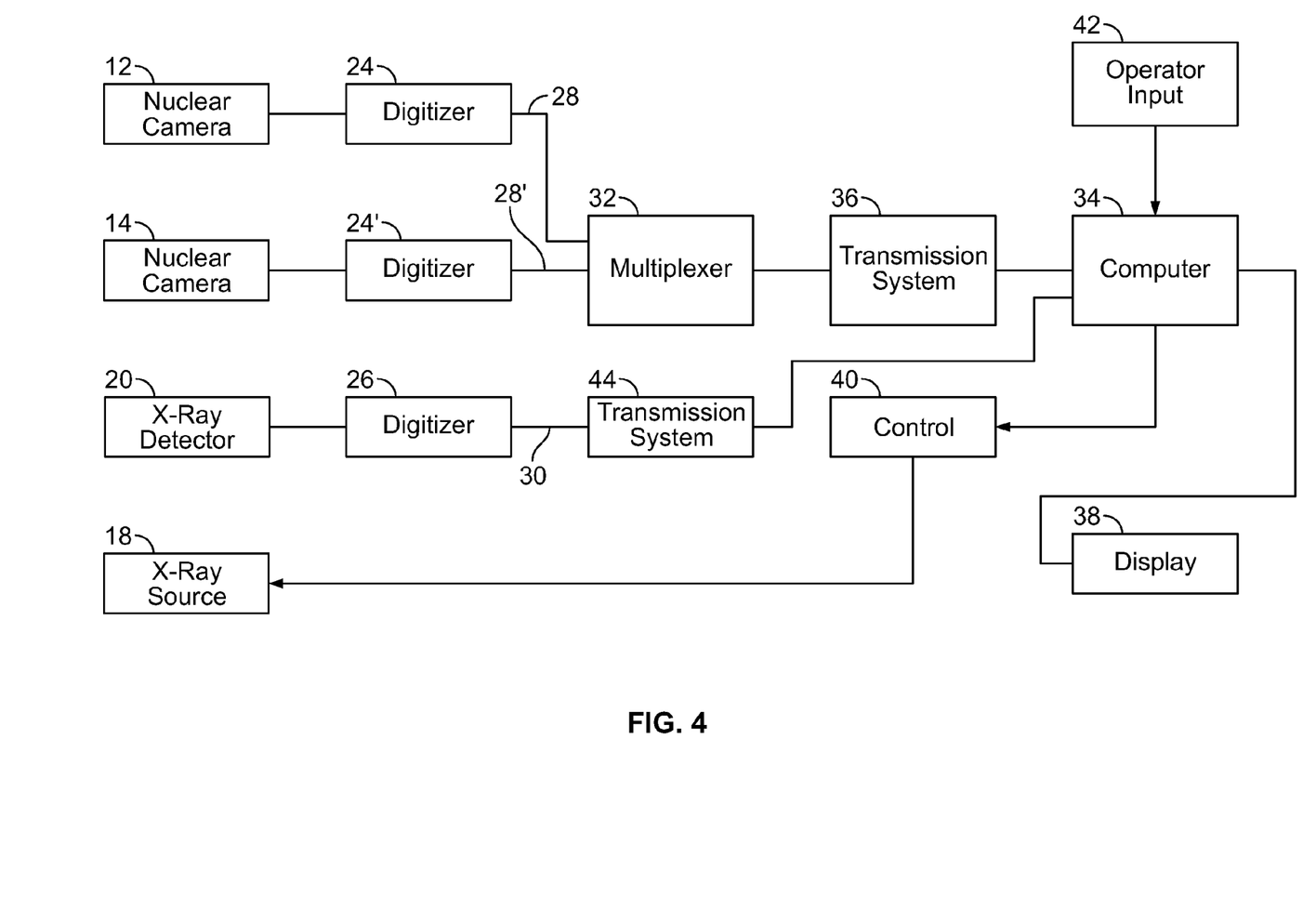
FIG. 4 is a block diagram showing circuitry for information transfer, control and image reconstruction of the system of FIGS. 1, 2 and 3 in accordance with an embodiment of the present invention.

Referring to FIG. 4, in one embodiment the nuclear energy signals and the X-ray signals are digitized in digitizers 24 (and 24') and 26, respectively, to produce digital signals on lines 28 (and 28') and 30 respectively. Digitizing by digitizers 24, 24' and 26 may be preceded by some signal processing and/or image pre-processing, as known in the art. The signals on lines 28 and 28' may be multiplexed (and optionally compressed) by a multiplexer 32 and fed to a computer 34 via a transmission system 36. The signals on line 30 are fed to the computer 34 via a different transmission system 44. Alternatively, one or both of the X-ray and emission data may be preprocessed in corresponding hardware/software prior to being fed into multiplexer 32 and/or transferred to the computer 34. It should be understood that in at least one of the embodiments positron emission tomography (PET) or single photon emission computed tomography (SPECT) imaging may be performed. In one embodiment, the NM imaging mode may be switched between PET and SPECT.

In computer 34, the signals are de-multiplexed (and if necessary, decompressed) as needed for processing (utilizing algorithms known in the art) to produce three dimensional (or two dimensional slice) images. These images may be displayed on a display 38, stored in a memory in the computer 34, or both. The nuclear images may be corrected for attenuation of intervening tissue and bones based on three-dimensional attenuation images produced from data generated from the transmission (X-ray) signals. Such correction may use algorithms known in the art.

In general, the nuclear medicine data may include raw data (the outputs of photomultiplier tubes or pixelized detectors of the camera heads) or calculated positions of detected nuclear events on the heads (either uncorrected positions or positions corrected for camera head distortions). In producing the nuclear image and the transmission (attenuation) image, the angular position of the camera heads 12 and 14 as well as the lineal position of the table 102 with respect to the heads 12 and 14, the X-ray source 18 and the detector 20 are taken into account by computer 34. These positions may be measured by transducers, encoders and the like.

In one embodiment, the same CPU and/or other hardware infrastructure may be used to generate both the nuclear medicine image and the attenuation image used to correct it. Alternatively or additionally, the same software may be used to generate the three dimensional nuclear medicine and attenuation images. In general, the reconstruction algorithms used for X-ray CT reconstruction and SPECT reconstruction may be the same or similar. Some types of PET reconstruction also use some of the same algorithms used for CT reconstruction. In general, use of the same hardware, and to some extent, of the same software, allows for a less expensive overall system cost.

In one embodiment, digitizers 24 and 24', lines 28 and 28' and multiplexer 32 may be mounted on a same moving portion of the gantry 46 while the digitizer 26 and line 30 are mounted on a different moving portion of the gantry 46. The transmission system 36 may be a retractor, such as having a coiled transmission line that winds and unwinds as the camera heads 12 and 14 are rotated about the central axis extending through the opening 22. In another embodiment, the transmission system 36 may be a slip ring system. Alternatively, the transmission system 36 may be a radio or optical link. The transmission system 44 (carrying signals associated with the X-ray source 18 and X-ray detector 20) may be a slip ring system. In general, a retractor is a simpler device in comparison with a slip ring, and is capable of rotating about the central axis for approximately one and a half revolutions in one direction, or about 540 degrees. The slip ring, in contrast, can rotate any number of times in either the clockwise or counter-clockwise directions.

The nuclear imaging signals and the X-ray signals may be acquired over different extents of the patient. For example, transmission data may be acquired only for axial slices for which significant nuclear activity is indicated or may be expected. For other slices, no attenuation correction data is acquired and the nuclear image is not corrected for attenuation. This more limited acquisition of transmission data means that the patient is irradiated by the X-rays for a shorter time and over a smaller portion of his body.

The portion of the patient's body over which transmission data should be acquired may be determined in a number of ways. For example, a low energy, one dimensional transmission X-ray "scout" image may be acquired to locate the position of an organ of interest. The scout image is "assembled" by computer 34 and displayed on display 38. An operator may indicate the extent of the organ, on the image, to computer 34. A controller 40 receives and is responsive to the commands from the computer 34, activating the X-ray source 18 only for those axial positions for which radiation is desired to correct for attenuation. The patient is thus irradiated with X-rays only over the axial extent of the organ or other region of interest.

Alternatively or additionally, the uncorrected nuclear image or a planar nuclear image is acquired first and displayed. The extent or region of nuclear activity is determined, either by the operator or automatically by the computer 34. A transmission image is then acquired as indicated above, only for this axial region. Alternatively, the nuclear data is analyzed for nuclear activity, on a slice by slice basis, to determine if transmission data is to be acquired.

Figure 5:
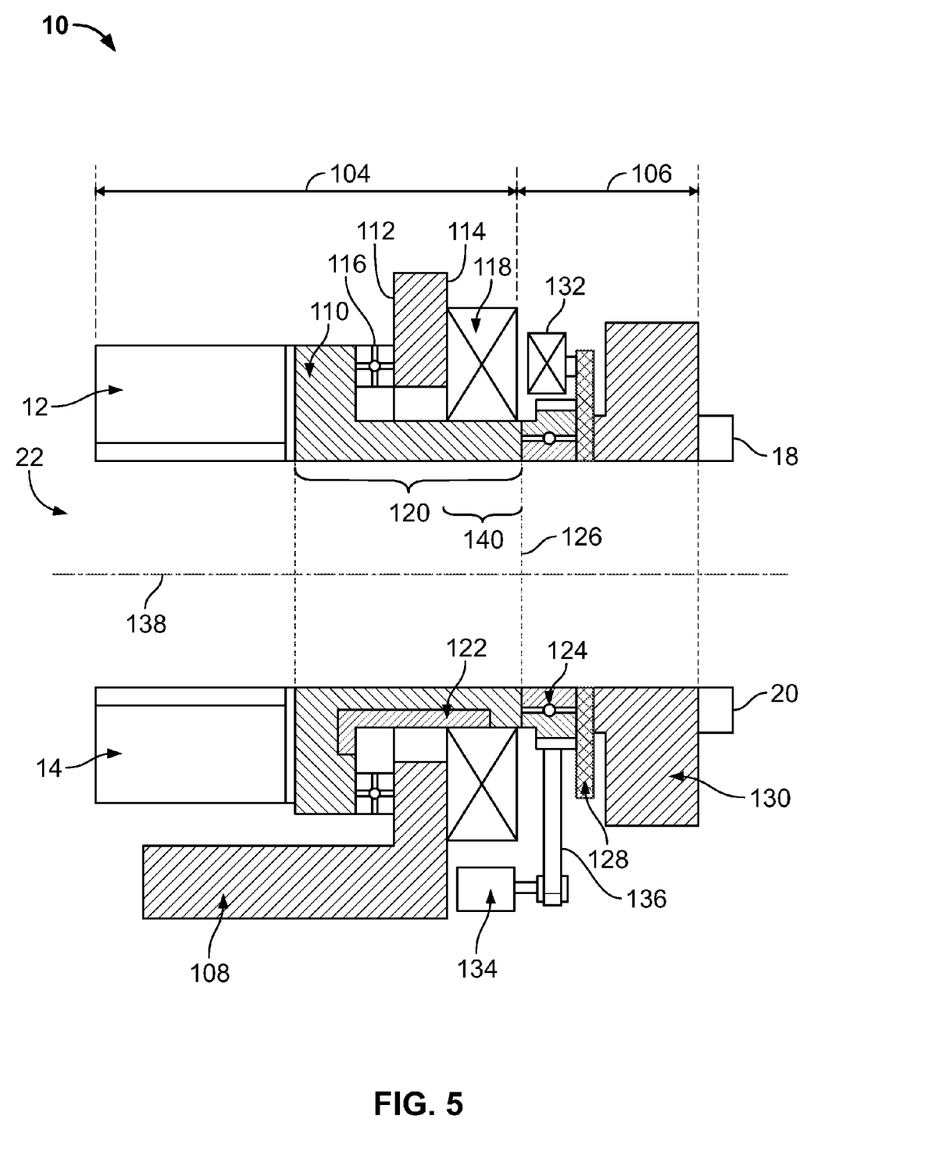
FIG. 5 illustrates a cross-sectional view of the imaging system that has a Nuclear Medicine portion and an AC portion formed in accordance with an embodiment of the present invention.

FIG. 5 illustrates a cross-sectional view of the imaging system 10 that has an NM portion 104 and an AC portion 106. The system 10 has the opening 22 through which the patient may be positioned and/or driven on the table 102 during scanning. A stator or stationary portion 108 is fixed to the floor. The stationary portion 108 may be somewhat "L" shaped and is configured to support both the NM portion 104 and the AC portion 106. Electronics, power and other processing capability may be housed within a cover that encloses the stationary portion 108. Therefore, power, electrical signals and/or imaging data are conveyed between the stationary portion 108 and two different rotating portions of the system 10. The camera heads 12 and 14 of the NM portion 104 and the X-ray source 18 and detector 20 of the AC portion 106 are aligned with respect to a central axis 138 that extends through the opening 22.

A rotor or NM rotating portion 110 is configured to extend through a front side 112 of the opening 22 of the stationary portion 108 and protrude beyond a back side 114, indicated as protruding portion 140. An NM bearing 116, such as a slewing bearing, connects the NM rotating portion 110 to the front side 112 of the stationary portion 108. The NM rotating portion 110 rotates on the NM bearing 116 and the NM bearing 116 supports the NM rotating portion 110. The camera heads 12 and 14 are mounted to the NM rotating portion 110. An NM retractor 118 is mounted to the protruding portion 140 of the NM rotating portion 110 proximate the back side 114 of the stationary portion 108. In another embodiment, an NM slip ring (not shown) may be used instead of the NM retractor 118. Cables 122 route power, image data and commands between the NM rotating portion 110 (and thus the camera heads 12 and 14) and the NM retractor 118.

The camera heads 12 and 14 include lead and/or other shielding material and are very heavy. The weight causes large moments on the NM bearing 116 and rotor or NM rotating portion 110, as well as the stator or stationary portion 108. Because the NM retractor 118 is mounted proximate the back side 114, arm 120 of the NM rotating portion 110 may be shorter compared to a configuration wherein the NM retractor 118 is mounted proximate the front side 112. The NM rotating portion 110 is therefore closer to the stationary portion 108, which in some embodiments may reduce the moments and improve sag, strength and balance of the NM portion 104 and/or the system 10. Additionally, in some embodiments the rigidity of the stationary portion 108 and the NM rotating portion 110 may be reduced, thus reducing the overall weight of the system 10 and the cost.

Additionally, by mounting the NM retractor 118 (or NM slip ring) proximate the back side 114 of the stationary portion 108, the NM retractor 118 may be more easily accessed for servicing. In another embodiment, the NM retractor 118 may be replaced (e.g. upgraded) by an NM slip ring after manufacturing without removing the camera heads 12 and 14. However, if already mounted to the system 10, in some embodiments portions of or the entire AC portion 106 may need to be removed prior to replacing the NM retractor 118 with an NM slip ring.

AC bearing 124, which may be a slewing bearing, is mounted to an outer end of protruding portion 140, corresponding to line 126, of the NM rotating portion 110. An AC rotor or AC rotating portion 130 is mounted to the AC bearing 124, and the X-ray source 18 and detector 20 are mounted on the AC rotating portion 130. Therefore, the NM rotating portion 110 supports the AC rotating portion 130. The AC rotating portion 130 rotates on the AC bearing 124, and thus the NM and AC rotating portions 110 and 130 may rotate separately with respect to each other. In another embodiment, the AC bearing 124 may be mounted to the NM retractor 118 or stationary portion 108, and thus the AC rotating portion 130 may be supported by the NM retractor 118 and the stationary portion 108 rather than the NM rotating portion 110.

Balance of the system 10 may be improved by positioning the camera heads 12 and 14 on an opposite side of the stationary portion 108 than the X-ray source 18 and the detector 20. Additionally, sag of the stationary portion 108 is reduced.

AC slip ring 128 is positioned between the AC bearing 124 and the AC rotating portion 130. The AC slip ring 128 is a large disc having a plurality of round conductors (e.g. rings) that are electrically connected to the AC rotating portion 130. A brush block 132 associated with the AC slip ring 128 is located proximate to the AC slip ring 128. The brush block 132 communicates power, image data, and commands to and from the round conductors. In one embodiment, the brush block 132 may be mounted on the NM rotating portion 110. In another embodiment, the brush block 132 may be mounted on the NM retractor 118 or the stationary portion 108. Communication between the brush block 132 (and thus the AC slip ring 128) and the stationary portion 108 is accomplished via cables (not shown).

A motor 134 and timing belt 136 are used to rotate the AC rotating portion 130. A different motor (not shown) is used to rotate the NM rotating portion 110. Because the connection between the NM and AC rotating portions 110 and 130 is accomplished through the AC bearing 124 (or alternatively, the AC bearing 124 is mounted to the NM retractor 118), the NM and AC rotating portions 110 and 130 can be rotated separately from each other and at different speeds. Also, the AC rotating portion 130 may be rotated at greater speeds than prior art configurations that use a single rotor or rotating portion for rotating the camera heads 12 and 14 and the X-ray or AC portion 106. Therefore, attenuation data may be acquired more quickly. In addition, the less expensive NM retractor 118 may be used rather than an NM slip ring as the heads 12 and 14 do not need to be rotated more than one full revolution during a scan.

In another embodiment, the NM portion 104 may be provided without the AC portion 106, functioning as a stand alone imaging device. The NM portion 104 may then, such as in the factory or in the field at a customer site, be retrofitted by adding the AC portion 106. It is not necessary to remove the camera heads 12 and 14 when adding the AC portion 106 to the system.

Figure 6:
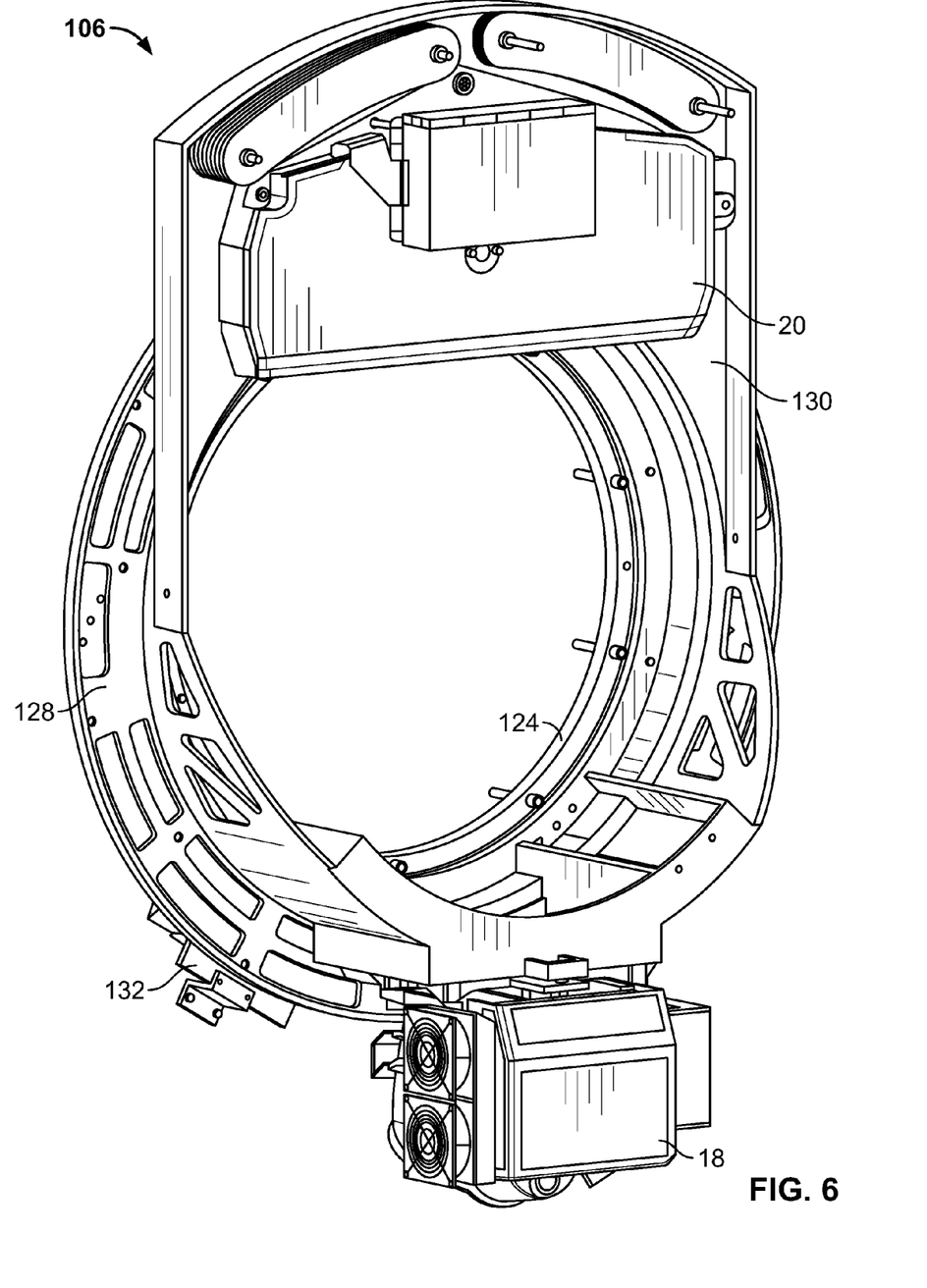
FIG. 6 illustrates a view of the AC portion of FIG. 5 formed in accordance with an embodiment of the present invention.

FIG. 6 illustrates an outer end of the AC portion 106. The X-ray source 18 and detector 20 are indicated as mounted on the AC rotating portion 130. The AC slip ring 128, brush block 132 and AC bearing 124 are also shown.

A technical effect of at least one embodiment is improving the sag, strength and stability of the system by mounting the camera heads and the NM retractor on opposite sides of the stator or stationary portion. Also, having the weight of the X-ray detector and X-ray source mounted on the opposite side of the stationary portion than the camera heads improves the balance of the system and may allow the stationary portion to be constructed of a lighter weight material or have overall less weight. The position of the NM retractor also enhances serviceability and access for upgrading the NM retractor to a slip ring. A single stationary portion is used. Using two different rotors or rotating portions allows the NM and AC portions of the system to be rotated at different speeds and independently of each other. In addition, the NM portion is configured to operate as a stand alone system or to be upgraded to the hybrid system by mounting the AC portion.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A nuclear medicine imaging system having attenuation correction, comprising:
    a stationary portion having front and back sides and an opening that extends between the front and back sides along a central axis;
    a nuclear medicine (NM) rotating portion rotatably mounted to the stationary portion, the NM rotating portion extending along the central axis from the front side of the stationary portion, through the opening, and projecting beyond the back side, at least one gamma camera head mounted on the NM rotating portion proximate the front side of the stationary portion and configured to be rotated about the central axis; and
    an attenuation correction (AC) rotating portion mounted proximate to the back side of the stationary portion, an X-ray source mounted on the AC rotating portion and configured to be rotated about the central axis.

2. The system of claim 1, wherein the AC rotating portion is mounted to the NM rotating portion, the AC rotating portion being spaced apart from the back side of the stationary portion.

3. The system of claim 2, further comprising one of an NM retractor or an NM slip ring mounted proximate to the back side of the stationary portion, said one of an NM retractor or an NM slip ring being located between the back side of the stationary portion and the AC rotating portion.

4. The system of claim 1, further comprising an AC bearing mounted to the NM rotating portion proximate the back side, the AC rotating portion being configured to be mounted to the AC bearing.

5. The system of claim 1, wherein the front and back sides face in opposite directions along the central axis, the system further comprising an NM bearing mounted to the front side of the stationary portion for interconnecting the NM rotating portion to the stationary portion.

6. The system of claim 1, further comprising one of an NM retractor or an NM slip ring mounted proximate to the back side of the stationary portion, and a communicative connection that is configured to route at least one of power, image data, or commands between the NM rotating portion on the front side of the stationary portion and said one of the NM retractor or NM slip ring.

7. The system of claim 1, further comprising an AC slip ring mounted between the X-ray source and the stationary portion, the AC slip ring configured to communicate at least one of power, image data, or commands between the AC rotating portion and a brush block.

8. The system of claim 1 further comprising an AC slip ring mounted between the X-ray source and the back side of the stationary portion, the AC slip ring comprising a brush block mounted on the NM rotating portion.

9. The system of claim 1, further comprising:
    an NM retractor mounted to the back side of the stationary portion; and
    an AC slip ring mounted between the X-ray source and the back side of the stationary portion, the AC slip ring comprising a brush block mounted on the NM retractor.

10. The system of claim 1, further comprising a motor configured to drive the AC rotating portion and another motor configured to drive the NM rotating portion.

11. The system of claim 1, wherein the front and back sides face in opposite directions along the central axis.

12. A nuclear medicine imaging system, comprising:
    a stationary portion having front and back sides and an opening that extends between the front and back sides along a central axis, the front and back sides facing in opposite directions along the central axis;
    a nuclear medicine (NM) rotating portion rotatably mounted to the stationary portion, the NM rotating portion extending from the front side through the opening of the stationary portion and having a protruding portion that projects beyond the back side along the central axis;
    at least one gamma camera head mounted on the NM rotating portion proximate to the front side of the stationary portion; and
    one of an NM retractor or an NM slip ring mounted proximate to the back side of the stationary portion.

13. The system of claim 12, further comprising:
    an AC rotating portion mounted to one of the stationary portion or the NM rotating portion; and
    an X-ray source and a detector mounted opposite each other on the AC rotating portion, the AC and NM rotating portions configured to be rotated about the central axis.

14. The system of claim 12, further comprising:
    an AC bearing mounted to the NM rotating portion; and
    an AC rotating portion configured to be mounted to the AC bearing.

15. The system of claim 12, further comprising:
    an AC bearing mounted to said one of the NM retractor or slip ring; and
    an AC rotating portion configured to be mounted to the AC bearing.

16. The system of claim 12, further comprising cables configured to route at least one of power, image data, or commands between the NM rotating portion on the front side of the stationary portion and said one of the NM retractor or NM slip ring.

17. The system of claim 12, further comprising:
    an AC rotating portion mounted proximate the back side of the stationary portion;
    an X-ray source and a detector mounted opposite each other on the AC rotating portion and configured to be rotated about a central axis; and
    said one of the NM retractor or slip ring mounted between the back side of the stationary portion and the X-ray source and detector.

18. A method for configuring a nuclear medicine imaging system having attenuation correction, comprising:
    mounting a nuclear medicine (NM) rotating portion on a front side of a stationary portion using an NM bearing, the stationary portion having an opening that extends between the front side and a back side of the stationary portion along a central axis, the NM rotating portion extending from the front side, through the opening, and projecting beyond the back side; and
    mounting an attenuation correction (AC) rotating portion proximate the back side of the stationary portion using an AC bearing, the AC rotating portion configured to be supported by one of the NM rotating portion or the stationary portion, the NM and AC rotating portions configured to rotate independently with respect to each other.

19. The method of claim 18, further comprising mounting one of an NM retractor or an NM slip ring between the stationary portion and the AC rotating portion.

20. The method of claim 18, further comprising:
mounting at least one camera head on the NM rotating portion; and
mounting an X-ray source and an X-ray detector on the AC rotating portion, the at least one camera head using a different transmission system than the X-ray source and the X-ray detector.

21. The method of claim 18, further comprising mounting a motor and a timing belt to the AC rotating portion, the motor and timing belt configured to drive the AC rotating portion separately with respect to the NM rotating portion.

* * * * *